United States Patent
Löffler et al.

(10) Patent No.: US 7,244,421 B2
(45) Date of Patent: *Jul. 17, 2007

(54) COSMETIC AND DERMATOLOGICAL HAIR-TREATMENT AGENTS

(75) Inventors: Matthlas Löffler, Niedernhausen (DE); Roman Morschhäuser, Mainz (DE); Jan Glauder, Frankfurt (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 228 days.

This patent is subject to a terminal disclaimer.

(21) Appl. No.: 10/433,117

(22) PCT Filed: Nov. 28, 2001

(86) PCT No.: PCT/EP01/13862

§ 371 (c)(1),
(2), (4) Date: Nov. 17, 2003

(87) PCT Pub. No.: WO02/43677

PCT Pub. Date: Jun. 6, 2002

(65) Prior Publication Data

US 2004/0115157 A1 Jun. 17, 2004

(30) Foreign Application Priority Data

Dec. 1, 2000 (DE) .............................. 100 59 827

(51) Int. Cl.
*A61K 7/06* (2006.01)
*C08L 33/00* (2006.01)

(52) U.S. Cl. ............... 424/70.16; 424/70.1; 424/70.2; 424/70.21; 514/937; 514/772.4; 526/288; 526/277; 526/250; 526/287

(58) Field of Classification Search ............... None
See application file for complete search history.

(56) References Cited

U.S. PATENT DOCUMENTS 2,826,551 A  3/1958  Geen ........................ 252/89
4,713,236 A  12/1987  Hoover et al. ................ 424/70
4,859,458 A  8/1989  Salamone et al. ............. 424/70
5,275,809 A  1/1994  Chen et al. .................... 424/70
5,879,718 A *  3/1999  Sebillote-Arnaud ........ 424/70.5
6,120,780 A *  9/2000  Dupuis et al. .............. 424/401
6,180,118 B1  1/2001  Maubru ....................... 424/401

FOREIGN PATENT DOCUMENTS

| DE | 199 07 715 | 8/2000 |
| EP | 0 181 773 | 5/1986 |
| EP | 0 503 853 | 9/1992 |
| EP | 0 815 828 | 1/1998 |
| EP | 0 815 844 | 1/1998 |
| EP | 0 829 258 | 3/1998 |

OTHER PUBLICATIONS

English Translationof International Preliminary Examination Report, PCT/EP01/13862, Dated Mar. 19, 2003.

* cited by examiner

*Primary Examiner*—Michael G. Hartley
*Assistant Examiner*—Jake M. Vu
(74) *Attorney, Agent, or Firm*—Richard P. Silverman

(57) ABSTRACT

The invention relates to cosmetic and dermatological hair treatment compositions comprising at least one copolymer. The copolymer is obtained by free-radical copolymerization of A) acryloyldimethyltaurine and/or acryloyldimethyltaurates, and
B) optionally, one or more further olefinically unsaturated, noncationic comonomers,
C) optionally, one or more olefinically unsaturated, cationic comonomers,
D) optionally, one or more silicon-containing component(s),
E) optionally, one or more fluorine-containing component(s),
F) optionally, one or more macromonomers,
G) optionally, the copolymerization taking place in the presence of at least one polymeric additive,
H) with the proviso that component A) is copolymerized with at least one component selected from one of the groups D) to G).

26 Claims, No Drawings

COSMETIC AND DERMATOLOGICAL HAIR-TREATMENT AGENTS

The present invention relates to cosmetic and dermatological hair treatment compositions comprising comb copolymers based on acryloyldimethyltaurine.

Frequent bleaching, perming, and coloring, but also regular washing of the hair with fat-removing surfactants, result in damage to the hair structure. The hair becomes brittle and loses its sheen. Roughened hair surfaces are a cause of matting and knotting of the hair, and combability is hindered. Consequently hair treatment compositions which enhance sheen, wet and dry combability, conditioning, and depth of color of the hair have acquired considerable importance. Furthermore, haircare compositions are intended to lower the heat load on the hair during blow drying, as a result of shorter drying times, and to "repair" existing hair damage, such as split ends, for example. Compositions of this kind are frequently distributed in the hair while it is still wet, after having been washed, in the form of a clear haircare rinse, an aerosol foam or else in emulsion form, as what are termed cream rinses, for example, and depending on the nature of the hair treatment composition are either rinsed out after a few minutes of exposure time, using water, or else are left on the hair.

The patent literature contains numerous proposals aimed at realizing such a project, including the use of water-soluble polymers, cationic fatty acid derivatives, principally cationic and especially quaternary ammonium compounds, such as cetyltrimethylammonium chloride, alone or in combination with various waxlike additions, such as hydrocarbons, fatty alcohols, and fatty acids, for example. Oils and oil-like substances as well, such as liquid hydrocarbon compounds, fatty alcohols, monocarboxy acid esters (monocarboxylic acid esters), polyalcohol esters, water-soluble silicones, and emulsions of silicones and other oils, are described.

A disadvantage of the agents described above is that after they have been rinsed off they often give the wet hair a sticky feel and make the dry hair heavy. Frequently utilized materials which give the hair a flexible and soft appearance are silicone derivatives. Silicones, however, have the drawback of making thin hair in particular so soft that it is virtually impossible to dress. Moreover, insoluble silicones, such as are proposed, for example, in U.S. Pat. No. 2,826,551, can often not be adequately incorporated into formulations. The problem here is to produce a suspension of the finely divided, insoluble polymers which ought to be stable over a relatively long period of time. A multiplicity of compounds have been added to the silicone-containing formulations in order to bring about thickening and stabilization. The most successful approach to date is described in EP 0,181,773, where the use of long-chain acyl derivatives leads to the formation of stable formulations. The acyl derivatives include fatty acid alkanol amides, fatty acid dialkanol amides, alkanol amides, and derivatives thereof. These amides are suspected of being involved in the formation of nitrosamines. It is therefore desirable to formulate cosmetic preparations without such derivatives.

Haircare compositions, moreover, must also have a viscosity which is adapted to the particular end use and is as variable as possible. For example, a hair gel or hair cure cream is required to have relatively high viscosities, whereas a hair rinse is commonly a runny liquid with a relatively low viscosity.

Known thickeners and gel formers include in particular the polyacrylic acids prepared on the basis of poly(meth)acrylic acid, and the water-soluble copolymers thereof. The diversity of the possible structures and the attendant diverse possibilities for application are manifested not least in a multiplicity of new patents filed worldwide from the mid-1970s on. A substantial drawback of these poly(meth)acrylic acid-based thickeners is the heavy pH dependence of the thickening performance. Thus in general viscosity is only developed when the pH of the formulation is set to a value above 6, so that the poly(meth)acrylic acid is in neutralized form. Furthermore, the corresponding gels/formulation are sensitive to UV radiation and shearing and give the skin and the hair a sticky feel as well. The handling of these thickener polymers is also deserving of improvement. Since the thickeners based on poly(meth)acrylic acid are generally present in acidic form, their formulation, for example, requires an additional neutralizing step.

In the 1990s, innovative thickeners based on crosslinked neutralized acryloyl-dimethyltaurates were introduced into the market (EP-B-0 815 828, EP-B-0 815 844, EP-B-0 815 845, and EP-B-0 829 258). In the form both of the preneutralized homopolymer and of the corresponding copolymer (®Aristoflex AVC, Clariant GmbH), these sulfonate group-based products are found superior to the poly(meth)acrylates in many respects. For example, acryloyldimethyltaurate-based thickener systems exhibit outstanding properties within pH ranges below pH 6, i.e., in a pH range within which it is no longer possible to operate with conventional poly(meth)acrylate thickeners. High UV and shear stability, outstanding viscoelastic properties, ease of processing, and a favorable toxicological profile of the principal monomer make acryloyldimethyltaurate-based thickener systems new, modern representatives with a high potential for the future.

Over the course of recent years a further thickener concept has become established on the market. By hydrophobic modification of the conventional poly(meth)acrylates an access route has been found here to polymers which may have both thickening and emulsifying/dispersing properties. Examples of commercially hydrophobically modified poly(meth)acrylates are ®Pemulen TR-1 and TR-2 from BF Goodrich and ®Aculyn 22 from Rohm & Haas. Since these hydrophobically modified polymers are without exception constructed on the basis of (meth)acrylic acid, they also possess the abovementioned disadvantages of the poly(meth)acrylates.

Surprisingly it has now been found that a new class of comb polymers based on acryloyldimethyltaurine (AMPS)—and suitable in the capacity of a conditioner, smoothener, antistat, bodying agent, emulsifier, dispersant, lubricant, and stabilizer—are outstandingly suitable for the formulation of cosmetic and dermatological hair treatment compositions.

The invention provides cosmetic and dermatological hair treatment compositions comprising at least one copolymer obtainable by free-radical copolymerization of A) acryloyldimethyltaurine and/or acryloyldimethyltaurates, B) if desired, one or more further olefinically unsaturated, noncationic, optionally crosslinking comonomers which have at least one oxygen, nitrogen, sulfur or phosphorus atom and possess a molecular weight of less than 500 g/mol, C) if desired, one or more olefinically unsaturated, cationic comonomers which have at least one oxygen, nitrogen, sulfur or phosphorus atom and possess a molecular weight of less than 500 g/mol, D) if desired, one or more silicon-containing components capable of free-radical polymerization and having a functionality of at least one, E) if desired, one or more fluorine-containing components capable of free-radical polymerization and having a functionality of at least one, F) if desired, one or more olefinically mono- or polyunsaturated, optionally crosslinking macromonomers each possessing at least one oxygen, nitrogen, sulfur or phosphorus atom and having a number-average molecular weight of greater than or equal to 200 g/mol, the macromonomers not being a silicon-containing component D) or fluorine-containing component E), G) the copolymerization taking place if desired in the presence of at least one polymeric additive having number-average molecular weights of from 200 g/mol to $10^9$ g/mol, H) with the proviso that component A) is copolymerized with at least one component selected from one of the groups D) to G).

The copolymers of the invention preferably possess a molecular weight of from $10^3$ g/mol to $10^9$ g/mol, more preferably from $10^4$ to $10^7$ g/mol, with particular preference from $5*10^4$ to $5*10^6$ g/mol.

The acryloyldimethlytaurates can be the organic or inorganic salts of acryloyldimethyltaurine (acrylamidopropyl-2-methyl-2-sulfonic acid). Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines may independently of one another be $(C_1–C_{22})$-alkyl radicals or $(C_2–C_{10})$-hydroxyalkyl radicals.

Preference is also given to mono- to triethoxylated ammonium compounds with different degrees of ethoxylation. It should be noted that mixtures of two or more of the abovementioned representatives are also embraced by the invention.

The degree of neutralization of the acryloyldimethyltaurine can be between 0 and 100%, with particular preference being given to a degree of neutralization of more than 80%.

Based on the total mass of the copolymers, the amount of acryloyldimethlytaurine and/or acryloyldimethyltaurates is at least 0.1% by weight, preferably from 20 to 99.5% by weight, more preferably from 50 to 98% by weight.

As comonomers B) it is possible to use all olefinically unsaturated noncationic monomers whose reaction parameters allow copolymerization with acryloyldimethyltaurine and/or acryloyldimethyltaurates in the respective reaction media. Preferred comonomers B) are unsaturated carboxylic acids and their anhydrides and salts, and also their esters with aliphatic, olefinic, cycloaliphatic, arylaliphatic or aromatic alcohols having a carbon number of from 1 to 30.

Particularly preferred unsaturated carboxylic acids are acrylic acid, methacrylic acid, styrenesulfonic acid, maleic acid, fumaric acid, crotonic acid, itaconic acid, and senecic acid.

Preferred counterions are $Li^+$, $Na^+$, $K^+$, $Mg^{++}$, $Ca^{++}$, $Al^{+++}$, $NH_4^+$, monoalkylammonium, dialkylammonium, trialkylammonium and/or tetraalkylammonium radicals, in which the alkyl substituents of the amines independently of one another can be $(C_1–C_{22})$-alkyl radicals or $(C_2–C_{10})$-hydroxyalkyl radicals. It is additionally possible to employ mono- to triethoxylated ammonium compounds with a different degree of ethoxylation. The degree of neutralization of the carboxylic acids can be between 0 and 100%.

Further preferred comonomers B) are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide, hydroxyethylmethacrylamide, hydroxypropylmethacrylamide, and mono [2-(methacryloyloxy)ethyl]succinate; N,N-dimethylamino methacrylate; diethylaminomethyl methacrylate; acrylamido- and methacrylamidoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable comonomers B) are inorganic acids and their salts and esters. Preferred acids are vinylphosphonic acid, vinylsulfonic acid, allylphosphonic acid, and methallylsulfonic acid.

The weight fraction of the comonomers B), based on the total mass of the copolymers, can be from 0 to 99.8% by weight and is preferably from 0.5 to 80% by weight, more preferably from 2 to 50% by weight.

Suitable comonomers C) include all olefinically unsaturated monomers with cationic charge which are capable of forming copolymers with acryloyldimethyltaurine or its salts in the chosen reaction media. The resulting distribution of the cationic charges across the chains can be random, alternating, blocklike or gradientlike. It may be noted that the cationic comonomers C) also comprehend those which bear the cationic charge in the form of a betaine, zwitterionic or amphoteric structure.

Comonomers C) for the purposes of the invention are also amino-functionalized precursors which can be converted by polymer-analogous reactions into their corresponding quaternary derivatives (e.g., reaction with dimethyl sulfate, methyl chloride), zwitterionic derivatives (e.g., reaction with hydrogen peroxide), betaine derivatives (e.g., reaction with chloroacetic acid), or amphoteric derivatives.

Particularly preferred comonomers C) are
diallyldimethylammonium chloride (DADMAC),
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride,
N-methyl-4-vinylpyridinium chloride,
dimethylaminoethyl methacrylate,
dimethylaminopropylmethacrylamide,
methacryloylethyl N-oxide and/or
methacryloylethylbetaine.

The weight fraction of the comonomers C), based on the total mass of the copolymers, can be from 0.1 to 99.8% by weight, more preferably from 0.5 to 30% by weight, and very preferably from 1 to 20% by weight.

Suitable polymerizable silicon-containing components D) are all compounds which are olefinically at least monounsaturated and capable of free-radical copolymerization under the reaction conditions chosen in each case. The distribution of the individual silicone-containing monomers across the polymer chains which form need not necessarily be random. The invention also embraces the formation, for example, of blocklike (including multiblock) or gradientlike structures. Combinations of two or more different silicone-containing representatives are also possible. The use of silicone-containing components having two or more polymerization-active groups leads to the construction of branched or crosslinked structures.

Preferred silicone-containing components D) are those of formula (I).

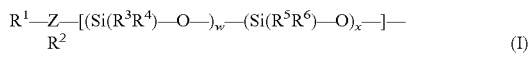

In this formula $R^1$ represents a polymerizable function from the group of the vinylically unsaturated compounds which is suitable for the synthesis of polymeric structures by a free-radical route. $R^1$ represents preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical.

The attachment of the silicone-containing polymer chain to the reactive end group $R^1$ requires a suitable chemical bridge Z. Preferred bridges Z are —O—, (($C_1$-$C_{50}$)alkylene), —(($C_6$-$C_{30}$)arylene)-, —(($C_5$-$C_8$)cycloalkylene)-, —(($C_1$-$C_{50}$) alkenylene)-, -(polypropylene oxide)$_n$-, -(polyethylene oxide)$_o$-, -(polypropylene oxide)$_n$(polyethylene oxide)$_o$-, where n and o independently of one another denote numbers from 0 to 200 and the distribution of the EO/PO units can be random or in the form of blocks. Further suitable bridge groups Z are —(($C_1$-$C_{10}$)alkyl)-(Si(OCH$_3$)$_2$)— and —(Si(OCH$_3$)$_2$)—.

The polymeric central moiety is represented by silicone-containing repeating units. The radicals $R^3$, $R^4$, $R^5$, and $R^6$ denote independently of one another —$CH_3$, —O—$CH_3$, —$C_6H_5$ or —O—$C_6H_5$.

The indices w and x represent stoichiometric coefficients which amount independently of one another to from 0 to 500, preferably 10 to 250.

The distribution of the repeating units across the chain can be not only purely random but also blocklike, alternating or gradientlike.

$R^2$ can first be an aliphatic, olefinic, cycloaliphatic, arylaliphatic or aromatic ($C_1$-$C_{50}$) hydrocarbon radical (linear or branched) or —OH, —$NH_2$, —$N(CH_3)_2$, —$R^7$ or stand for the structural unit [—Z—$R^1$]. The definition of the two variables Z and $R^1$ has already been explained. $R^7$ stands for further Si-containing groups. Preferred $R^7$ radicals are —O—Si($CH_3$)$_3$, —O—Si(Ph)$_3$, —O—Si(O—Si($CH_3$)$_3$)$_2$CH$_3$) and —O—Si(O—Si(Ph)$_3$)$_2$Ph).

If $R^2$ is an element of the group [—Z—$R^1$] the monomers in question are difunctional monomers which can be used to crosslink the polymer structures which form. Formula (I) describes not only silicone-containing polymer species with vinylic functionalization and a polymer-typical distribution, but also defined compounds having discrete molecular weights.

Particularly preferred silicone-containing components are the following components with acrylic or methacrylic modification:

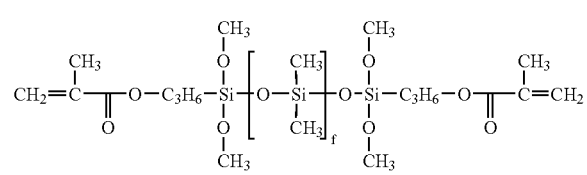

methacryloyloxypropyldimethlsilyl-endblocked polydimethylsiloxanes (f=2 to 500)

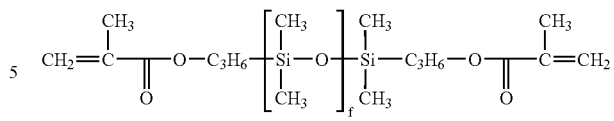

methacryloyloxypropyl-endblocked polydimethylsiloxanes (f=2 to 500)

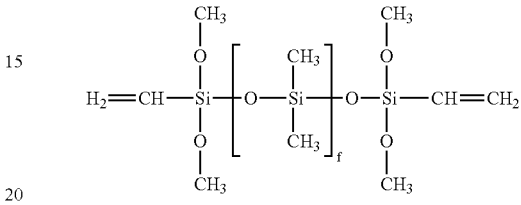

vinyldimethoxysilyl-endblocked polydimethylsiloxanes (f=2–500)

Based on the total mass of the copolymers, suitable silicon-containing components can be present in an amount of up to 99.9% by weight, preferably from 0.5 to 30% by weight, more preferably from 1 to 20% by weight.

Suitable polymerizable fluorine-containing components E) include all compounds which are olefinically at least monounsaturated and which are capable of free-radical copolymerization under the reaction conditions chosen in each case. The distribution of the individual fluorine-containing monomers across the polymer chains which form need not necessarily be random. The invention also embraces the formation of blocklike (including multiblock) or gradientlike structures, for example. Combinations of two or more different fluorine-containing components E) are also possible, it being clear to the expert that monofunctional representatives lead to the formation of comb-shaped structures while di-, tri-, or polyfunctional components E) lead to structures which are at least partly crosslinked.

Preferred fluorine-containing components E) are those of formula (II).

In this formula $R^1$ represents a polymerizable function from the group of the vinylically unsaturated compounds which is suitable for the construction of polymeric structures by a free-radical route. $R^1$ is preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical, more preferably an acryloyl or methacryloyl radical.

The attachment of the fluorine-containing group to the reactive end group $R^1$ requires a suitable chemical bridge Y. Preferred bridges Y are —O—, —C(O)—, —C(O)—O—, —S—, —O—$CH_2$—CH(O—)—$CH_2$OH, —O—$CH_2$—CH(OH)—$CH_2$—O—, —O—$SO_2$—O—, —O—S(O)—O—, —PH—, —P($CH_3$)—, —$PO_3$—, —NH—, —N($CH_3$)—, —O—($C_1$-$C_{50}$)alkyl-O—, —O-phenyl-O—, —O-benzyl-O—, —O—($C_5$-$C_8$)cycloalkyl-O—, —O—($C_1$-$C_{50}$)alkenyl-O—, —O—(CH($CH_3$)—$CH_2$—O)$_n$—, —O—($CH_2$—$CH_2$—O)$_n$—, and —O—([CH—$CH_2$—O]$_n$—[$CH_2$—$CH_2$—O]$_m$)$_o$—, where n, m, and o independently of one another denote numbers from 0 to 200 and the distribution of the EO and PO units can be random or in the form of blocks. r and s are stoichiometric coefficients which independently of one another denote numbers from 0 to 200.

Preferred fluorine-containing components E) of formula (II) are
perfluorohexylethanol methacrylate,
perfluorohexoylpropanol methacrylate,
perfluoroctylethanol methacrylate,
perfluoroctylpropanol methacrylate,
perfluorohexylethanolyl polyglycol ether methacrylate,
perfluorohexoylpropanolyl poly[ethylglycol-co-propylene glycol ether]acrylate,
perfluoroctylethanolyl poly[ethylglycol-block-co-propylene glycol ether]methacrylate,
perfluoroctylpropanolyl polypropylene glycol ether methacrylate.

Based on the total mass of the copolymers the amount of fluorine-containing components can be up to 99.9% by weight, preferably from 0.5 to 30% by weight, more preferably from 1 to 20% by weight.

The macromonomers F) are at least singly olefinically functionalized polymers having one or more discrete repeating units and a number-average molecular weight of greater than or equal to 200 g/mol. In the copolymerization it is also possible to use mixtures of chemically different macromonomers F). The macromonomers are polymeric structures composed of one or more repeating units and have a molecular weight distribution characteristic of polymers. Preferred macromonomers F) are compounds of formula (III).

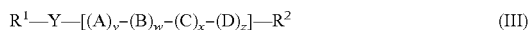

$R^1$ represents a polymerizable function from the group of the vinylically unsaturated compounds which are suitable for constructing polymeric structures by a free-radical route. Preferably $R^1$ is a vinyl, allyl, methallyl, methylvinyl, acryloyl ($CH_2=CH-CO-$), methacryloyl ($CH_2=C[CH_3]-CO-$), crotonyl, senecionyl, itaconyl, maleyl, fumaryl or styryl radical.

Attachment of the polymer chain to the reactive end group requires a suitable bridging group Y. Preferred bridges Y are $-O-$, $-C(O)-$, $-C(O)-O-$, $-S-$, $-O-CH_2-CH(O-)-CH_2OH$, $-O-CH_2-CH(OH)-CH_2O-$, $-O-SO_2-O-$, $-O-SO_2-O-$, $-O-SO-O-$, $-PH-$, $-P(CH_3)-$, $-PO_3-$, $-NH-$, and $-N(CH_3)-$, more preferably $-O-$.

The polymeric central moiety of the macromonomer is represented by the discrete repeating units A, B, C, and D. Preferred repeating units A, B, C, and D are derived from acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

The indices v, w, x, and z in formula (III) represent the stoichiometric coefficients relating to the repeating units A, B, C, and D. v, w, x, and z amount independently of one another to from 0 to 500, preferably 1 to 30, it being necessary for the sum of the four coefficients on average to be $\geq 1$.

The distribution of the repeating units over the macromonomer chain can be random, blocklike, alternating or gradientlike.

$R^2$ denotes a linear or branched aliphatic, olefinic, cycloaliphatic, arylaliphatic or aromatic ($C_1$–$C_{50}$) hydrocarbon radical, OH, $-NH_2$, $-N(CH_3)_2$ or is the structural unit $[-Y-R^1]$.

In the case of $R^2$ being $[-Y-R^1]$ the macromonomers in question are difunctional and suitable for crosslinking the copolymers.

Particularly preferred macromonomers F) are acrylically or methacrylically monofunctionalized alkyl ethoxylates of formula (IV).

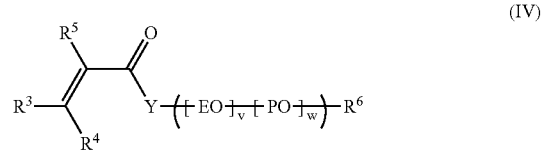

$R^3$, $R^4$, $R^5$, and $R^6$ are independently of one another hydrogen or n-aliphatic, iso-aliphatic, olefinic, cycloaliphatic, arylaliphatic or aromatic ($C_1$–$C_{30}$) hydrocarbon radicals.

Preferably $R^3$ and $R^4$ are H or $-CH_3$, more preferably H; $R^5$ is H or $-CH_3$; and $R^6$ is an n-aliphatic, iso-aliphatic, olefinic, cycloaliphatic, arylaliphatic or aromatic ($C_1$–$C_{30}$) hydrocarbon radical.

v and w are in turn the stoichiometric coefficients relating to the ethylene oxide units (EO) and propylene oxide units (PO). v and w amount independently of one another to from 0 to 500, preferably 1 to 30, it being necessary for the sum of v and w to be on average $\geq 1$. The distribution of the EO and PO units over the macromonomer chain can be random, blocklike, alternating or gradientlike. Y stands for the abovementioned bridges.

Further particularly preferred macromonomers F) have the following structure in accordance with formula (IV):

| Name | $R^3$ | $R^4$ | $R^5$ | $R^6$ | v | w |
|---|---|---|---|---|---|---|
| ® LA-030 methacrylate | H | H | $-CH_3$ | -lauryl | 3 | 0 |
| ® LA-070 methacrylate | H | H | $-CH_3$ | -lauryl | 7 | 0 |
| ® LA-200 methacrylate | H | H | $-CH_3$ | -lauryl | 20 | 0 |
| ® LA-250 methacrylate | H | H | $-CH_3$ | -lauryl | 25 | 0 |
| ® T-080 methacrylate | H | H | $-CH_3$ | -talc | 8 | 0 |
| ® T-080 acrylate | H | H | H | -talc | 8 | 0 |
| ® T-250 methacrylate | H | H | $-CH_3$ | -talc | 25 | 0 |
| ® T-250 crotonate | $-CH_3$ | H | $-CH_3$ | -talc | 25 | 0 |
| ® OC-030 methacrylate | H | H | $-CH_3$ | -octyl | 3 | 0 |
| ® OC-105 methacrylate | H | H | $-CH_3$ | -octyl | 10 | 5 |
| ® Behenyl-010-methylaryl | H | H | H | -behenyl | 10 | 0 |
| ® Behenyl-020-methylaryl | H | H | H | -behenyl | 20 | 0 |
| ® Behenyl-010-senecionyl | $-CH_3$ | $-CH_3$ | H | -behenyl | 10 | 0 |
| ® PEG-440 diacrylate | H | H | H | -acryloyl | 10 | 0 |
| ® B-11-50 methacrylate | H | H | $-CH_3$ | -butyl | 17 | 13 |
| ® MPEG-750 methacrylate | H | H | $-CH_3$ | -methyl | 18 | 0 |
| ® P-010 acrylate | H | H | H | -phenyl | 10 | 0 |
| ® O-050 acrylate | H | H | H | -oleyl | 5 | 0 |

Further particularly suitable macromonomers F) are esters of (meth)acrylic acid with
($C_{10}$–$C_{18}$) fatty alcohol polyglycol ethers having 8 EO units (Genapol® C-080)

$C_{11}$ oxo alcohol polyglycol ethers having 8 EO units (Genapol® UD-080)

($C_{12}$–$C_{14}$) fatty alcohol polyglycol ethers having 7 EO units (Genapol® LA-070)

($C_{12}$–$C_{14}$) fatty alcohol polyglycol ethers having 11 EO units (Genapol® LA-110)

($C_{16}$–$C_{18}$) fatty alcohol polyglycol ethers having 8 EO units (Genapol® T-080)

($C_{16}$–$C_{18}$) fatty alcohol polyglycol ethers having 15 EO units (Genapol® T-150)

($C_{16}$–$C_{18}$) fatty alcohol polyglycol ethers having 11 EO units (Genapol® T-110)

($C_{16}$–$C_{18}$) fatty alcohol polyglycol ethers having 20 EO units (Genapol® T-200)

($C_{16}$–$C_{18}$) fatty alcohol polyglycol ethers having 25 EO units (Genapol® T-250)

($C_{18}$–$C_{22}$) fatty alcohol polyglycol ethers having 25 EO units and/or iso-($C_{16}$–$C_{18}$) fatty alcohol polyglycol ethers having 25 EO units.

The Genapol® grades are products of Clariant GmbH.

The molecular weight of the macromonomers F) is preferably from 200 g/mol to $10^6$ g/mol, more preferably from 150 to $10^4$ g/mol, and very preferably from 200 to 5 000 g/mol.

Based on the total mass of the copolymers it is possible to use suitable macromonomers at up to 99.9% by weight. The ranges used are preferably from 0.5 to 30% by weight and from 70 to 99.5% by weight. Particularly preferred are fractions of from 1 to 20% by weight and from 75 to 95% by weight.

Preferred copolymers are those obtainable by copolymerizing at least components A), C), and D).

Further preferred copolymers are those obtainable by copolymerizing at least components A), C), and E).

Further preferred copolymers are those obtainable by copolymerizing at least components A), C), and F).

Further preferred copolymers are those obtainable by copolymerizing at least components A), D), and F).

Further preferred copolymers are those obtainable by copolymerizing at least components A) and F).

Further preferred copolymers are those obtainable by copolymerizing at least components A) and D).

Further preferred copolymers are those obtainable by copolymerizing at least components A) and E).

In one preferred embodiment the copolymerization is conducted in the presence of at least one polymeric additive G), the additive G) being added wholly or partly in solution to the polymerization medium before the actual copolymerization. The use of two or more additives G) is likewise in accordance with the invention.

Crosslinked additives G) may likewise be used.

The additives G) or mixtures thereof must only be wholly or partly soluble in the chosen polymerization medium. During the actual polymerization step the additive G) has a number of functions. On the one hand it prevents the formation of overcrosslinked polymer fractions in the copolymer which forms in the actual polymerization step, and on the other hand the additive G) is statistically attacked by active free radicals in accordance with the very well-known mechanism of graft copolymerization. Depending on the particular additive G), this results in greater or lesser fractions of the additive being incorporated into the copolymers. Moreover, suitable additives G) possess the property of altering the solution parameters of the copolymers which form during the free-radical polymerization reaction in such a way that the average molecular weights are shifted to higher values. As compared with analogous copolymers prepared without the addition of the additives G), those prepared with the addition of additives G) advantageously exhibit a significantly higher viscosity in aqueous solution.

Preferred additives G) are homopolymers and copolymers which are soluble in water and/or alcohols, preferably in t-butanol. The term "copolymers" also comprehends those having more than two different monomer types.

Particularly preferred additives G) are homopolymers and copolymers of N-vinylformamide, N-vinylacetamide, N-vinylpyrrolidone, ethylene oxide, propylene oxide, acryloyldimethlytaurine, N-vinylcaprolactam, N-vinylmethylacetamide, acrylamide, acrylic acid, methacrylic acid, N-vinylmorpholide, hydroxyethyl methacrylate, diallyldimethylammonium chloride (DADMAC) and/or [2-(methacryloyloxy)ethyl]trimethylammonium chloride (MAPTAC); polyalkylene glycols and/or alkylpolyglycols.

Particularly preferred additives G) are polyvinylpyrrolidones (e.g., Luviskol K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives G) is preferably from $10^2$ to $10^7$ g/mol, more preferably from $0.5*10^4$ to $10^6$ g/mol.

The amount in which the polymeric additive G) is used, based on the total mass of the monomers to be polymerized during the copolymerization, is preferably from 0.1 to 90% by weight, more preferably from 1 to 20% by weight, and with particular preference from 1.5 to 10% by weight.

In another preferred embodiment the copolymers of the invention are crosslinked, i.e., they contain comonomers having at least two polymerizable vinyl groups. Preferred crosslinkers are methylenebisacrylamide; methylenebismethacrylamide; esters of unsaturated monocarboxylic and polycarboxylic acids with polyols, preferably diacrylates and triacrylates, dimethacrylates and trimethacrylates, more preferably butanediol and ethylene glycol diacrylate and methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives. A particularly preferred crosslinker is trimethylolpropane triacrylate (TMPTA). The weight fraction of crosslinking comonomers, based on the total mass of the copolymers, is preferably up to 20% by weight, more preferably from 0.05 to 10% by weight, and very preferably from 0.1 to 7% by weight.

The polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electromagnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide or azo initiators, such as azodiisobutyronitrile (AIBN), for example.

Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate, etc.) or redox systems comprising as reducing component an aliphatic or aromatic sulfonic acid (e.g., benzenesulfonic acid, toluenesulfonic acid, etc.).

Serving as the polymerization medium may be any solvents which are very substantially inert in respect of free-radical polymerization reactions and which allow the development of high molecular weights. Use is preferably made of water and lower, tertiary alcohols or hydrocarbons having 3 to 30 carbon atoms. In one particularly preferred embodiment t-butanol is used as the reaction medium. Mixtures of two or more representatives of the potential solvents described are of course likewise in accordance with the invention. This also includes emulsions of mutually immiscible solvents (e.g., water/hydrocarbons). In principle, all kinds of reaction regime leading to the polymer structures of the invention are suitable (solution polymerization, emulsion methods, precipitation methods, high-pressure methods, suspension methods, bulk polymerization, gel polymerization, and so on). Preferred suitability is possessed by precipitation polymerization, particularly preferred suitability by precipitation polymerization in tert-butanol. The following list shows 67 copolymers with particular suitability for formulating the compositions of the invention. The different copolymers 1 to 67 are obtainable in accordance with the following preparation processes 1, 2, 3, and 4.

Process 1:

These polymers can be prepared by the precipitation method in tert-butanol. The monomers were introduced in t-butanol, the reaction mixture was rendered inert, and then, after initial heating to 60° C., the reaction was initiated by addition of the corresponding t-butanol-soluble initiator (preferably dilauroyl peroxide). After the end of reaction (2 hours) the polymers were isolated by removal of the solvent under suction and by subsequent vacuum drying.

Process 2:

These polymers are preparable by the gel polymerization method in water. The monomers are dissolved in water, the reaction mixture is rendered inert, and then, after initial heating to 65° C., the reaction is initiated by addition of suitable initiators or initiator systems (preferably $Na_2S_2O_8$). The polymer gels are subsequently comminuted and the polymers are isolated after drying.

Process 3:

These polymers are preparable by the emulsion method in water. The monomers are emulsified in a mixture of water/organ solvent (preferably cyclohexane) using an emulsifier, the reaction mixture is rendered inert by means of $N_2$, and then, after initial heating to 80° C., the reaction is initiated by addition of suitable initiators or initiator systems (preferably $Na_2S_2O_8$). The polymer emulsions are subsequently evaporated down (with cyclohexane acting as an azeotrope former for water) and the polymers are thereby isolated.

Process 4:

These polymers are preparable by the solution method in organic solvents (preferably toluene, also, for example, tertiary alcohols). The monomers are introduced in the solvent, the reaction mixture is rendered inert, and then, after initial heating to 70° C., the reaction is initiated by addition of suitable initiators or initiator systems (preferably dilauroyl peroxide). The polymers are isolated by evaporating off the solvent and by subsequent vacuum drying.

Polymers having hydrophobic side chains, uncrosslinked

| No. | Composition | Preparation process |
|---|---|---|
| 1 | 95 g AMPS 5 g Genapol T-080 | 1 |
| 2 | 90 g AMPS 10 g Genapol T-080 | 1 |
| 3 | 85 g AMPS 15 g Genapol T-080 | 1 |
| 4 | 80 g AMPS 20 g Genapol T-080 | 1 |
| 5 | 70 g AMPS 30 g Genapol T-080 | 1 |
| 6 | 50 g AMPS 50 g Genapol T-080 | 3 |
| 7 | 40 g AMPS 60 g Genapol T-080 | 3 |
| 8 | 30 g AMPS 70 g Genapol T-080 | 3 |
| 9 | 20 g AMPS 80 g Genapol T-080 | 3 |
| 10 | 60 g AMPS 60 g BB10 | 4 |
| 11 | 80 g AMPS 20 g BB10 | 4 |
| 12 | 90 g AMPS 10 g BB10 | 3 |
| 13 | 80 g AMPS 20 g BB10 | 1 |
| 14 | 80 g AMPS 20 g Genapol LA040 | 1 |

Polymers having hydrophobic side chains, crosslinked

| No. | Composition | Preparation process |
|---|---|---|
| 15 | 80 g AMPS 20 g Genapol LA040 0.6 g AMA | 1 |
| 16 | 80 g AMPS 20 g Genapol LA040 0.8 g AMA | 1 |
| 17 | 80 g AMPS 20 g Genapol LA040 1.0 g AMA | 1 |
| 18 | 628.73 g AMPS 120.45 g Genapol T-250 6.5 g TMPTA | 2 |
| 19 | 60 g AMPS 40 g BB10 1.9 g TMPTA | 4 |
| 20 | 80 g AMPS 20 g BB10 1.4 g TMPTA | 4 |
| 21 | 90 g AMPS 10 g BB10 1.9 g TMPTA | 4 |
| 22 | 80 g AMPS 20 g BB10 1.9 g TMPTA | 4 |
| 23 | 60 g AMPS 40 g BB10 1.4 g TMPTA | 4 |

Polymers having hydrophobic side chains, crosslinked, grafted

| No. | Composition | Preparation process |
|---|---|---|
| 24 | 95 g AMPS 5 g BB10, 1.9 g TMPTA, 1 g Poly-NVP | 1 |
| 25 | 90 g AMPS 10 g BB10, 1.9 g TMPTA, 1 g Poly-NVP | 1 |
| 26 | 85 g AMPS 15 g BB10, 1.9 g TMPTA, 1 g Poly-NVP | 1 |
| 27 | 90 g AMPS 10 g BB10, 1.9 g TMPTA, 1 g Poly-NVP | 1 |

Polymers having silicon-containing groups, uncrosslinked

| No. | Composition | Preparation process |
|---|---|---|
| 28 | 80 g AMPS, 20 g Silvet 867 | 1 |
| 29 | 80 g AMPS, 50 g Silvet 867 | 4 |

Polymers having silicon-containing groups, crosslinked

| No. | Composition | Preparation process |
|---|---|---|
| 30 | 80 g AMPS, 20 g Silvet 867, 0.5 g MBA | 4 |
| 31 | 80 g AMPS, 20 g Silvet 867, 1.0 g MBA | 1 |
| 32 | 60 g AMPS, 40 g Y-12867, 0.95 g AMA | 1 |
| 33 | 80 g AMPS, 20 g Y-12867, 0.95 g AMA | 1 |
| 34 | 90 g AMPS, 10 g Y-12867, 0.95 g AMA | 1 |
| 35 | 60 g AMPS, 40 g Silvet 7280, 0.95 g AMA | 1 |
| 36 | 80 g AMPS, 20 g Silvet 7280, 0.95 g AMA | 1 |
| 37 | 90 g AMPS, 10 g Silvet 7280, 0.95 g AMA | 1 |
| 38 | 60 g AMPS, 40 g Silvet 7608, 0.95 g AMA | 1 |
| 39 | 80 g AMPS, 20 g Silvet 7608, 0.95 g AMA | 1 |
| 40 | 90 g AMPS, 10 g Silvet 7608, 0.95 g AMA | 1 |

Polymers having hydrophobic side chains and cationic groups, uncrosslinked

| No. | Composition | Preparation process |
|---|---|---|
| 41 | 87.5 g AMPS, 7.5 g Genapol T-110, 5 g DADMAC | 2 |
| 42 | 40 g AMPS, 10 g Genapol T110, 45 g methacrylamide | 2 |
| 43 | 55 g AMPS, 40 g Genapol LA040, 5 g Quat | 1 |
| 44 | 75 g AMPS, 10 g BB10, 6.7 g Quat | 1 |

Polymers having hydrophobic side chains and cationic groups, crosslinked

| No. | Composition | Preparation process |
|---|---|---|
| 45 | 60 g AMPS, 20 g Genapol T-80, 10 g Quat, 10 g HEMA | 1 |
| 46 | 75 g AMPS, 20 g Genapol T-250, 5 g Quat, 1.4 g TMPTA | 1 |
| 47 | 75 g AMPS, 20 g Genapol T-250, 10 g Quat, 1.4 g TMPTA | 1 |
| 48 | 75 g AMPS, 20 g Genapol T-250, 20 g Quat, 1.4 g TMPTA | 1 |

Polymers having fluorine-containing groups

| No. | Composition | Preparation process |
|---|---|---|
| 49 | 94 g AMPS, 2.02 g Fluowet AC 600 | 1 |
| 50 | 80 g AMPS, 20 g perfluorooctylpolyethylene glycol methacrylate, 1 g Span 80 | 3 |

Polymers having fluorine-containing groups, grafted

| No. | Composition | Preparation process |
|---|---|---|
| 51 | 80 g AMPS, 10 g Fluowet AC 600, 5 g Poly-NVP | 1 |
| 52 | 70 g AMPS, 8 g perfluorooctylethyloxyglyceryl methacrylate, 5 g Poly-NVP | 4 |

Polyfunctional polymers

| No. | Composition | Preparation process |
|---|---|---|
| 53 | 80 g AMPS, 10 g Genapol LA070, 10 g Silvet 7608, 1.8 g TMPTA | 1 |
| 54 | 70 g AMPS, 5 g N-vinylpyrrolidone, 15 g Genapol T-250 methacrylate, 10 g Quat, 10 g Poly-NVP | 4 |
| 55 | 80 g AMPS, 5 g N-vinylformamide, 5 g Genapol O-150 methacrylate, 10 g DADMAC, 1.8 g TMPTA, 8 g poly-N-vinylformamide | 2 |
| 56 | 70 g AMPS, 5 g N-vinylpyrrolidone, 15 g Genapol T-250 methacrylate, 10 g Quat, 10 g Poly-NVP | 1 |
| 57 | 60 g AMPS, 10 g Genapol-BE-020 methacrylate, 10 g Genapol T-250 acrylate, 20 g Quat, 1 g Span 80 | 1 |
| 58 | 60 g AMPS, 20 g MPEG-750 methacrylate, 10 g methacryloyloxypropyldimethicone, 10 g perfluorooctylpolyethylene glycol methacrylate, 10 g poly[N-vinylcaprolactone-co-acrylic acid] (10/90) | 1 |
| 59 | 80 g AMPS, 5 g N-vinylformamide, 5 g Genapol O-150 methacrylate, 10 g DADMAC, 1.8 g TMPTA | 1 |
| 60 | 70 g AMPS, 10 g Genapol T-250 acrylate, 5 g N-methyl-4-vinylpyridinium chloride, 2.5 g Silvet Y-12867, 2.5 g perfluorohexylpolyethylene glycol methacrylate, 10 g polyethylene glycol dimethacrylate, 4 g poly[N-vinylcaprolactam] | 1 |
| 61 | 10 g AMPS, 20 g acrylamide, 30 g N-2-vinylpyrrolidone, 20 g Silvet 7608, 10 g methacryloyloxypropyldimethicone, 10 g Fluowet AC 812 | 3 |
| 62 | 60 g AMPS, 10 g DADMAC, 10 g Quat, 10 g Genapol-LA-250 crotonate, 10 g methacryloyloxypropyldimethicone, 7 g poly[acrylic acid-co-N-vinylformamide] | 1 |
| 63 | 50 g AMPS, 45 g Silvet 7608, 1.8 g TMPTA, 8 g poly[N-vinylformamide] | 1 |

-continued

| No. | Composition | Preparation process |
|---|---|---|
| 64 | 20 g AMPS, 10 g Genapol T 110, 35 g MAA, 30 g HEMA, 5 g DADMAC | 4 |
| 65 | 20 g AMPS, 80 g BB10, 1.4 g TMPTA | 1 |
| 66 | 75 g AMPS, 20 g BB10, 6.7 g Quat, 1.4 g TMPTA | 1 |
| 67 | 35 g AMPS, 60 g acrylamide, 2 g VIFA, 2.5 g vinylphosphonic acid, 2 mol % Fluowet EA-600 | 4 |

Chemical designation of the reactants:

| | |
|---|---|
| AMPS | acryloyldimethyltaurate, either Na or NH4 salt |
| Genapol ® T-080 | $C_{16}$–$C_{18}$ fatty alcohol polyglycol ether having 8 EO units |
| Genapol ® T-110 | $C_{12}$–$C_{14}$ fatty alcohol polyglycol ether having 11 EO units |
| Genapol ® T-250 | $C_{16}$–$C_{18}$ fatty alcohol polyglycol ether having 25 EO units |
| Genapol ® LA-040 | $C_{12}$–$C_{14}$ fatty alcohol polyglycol ether having 4 EO units |
| Genapol ® LA-070 | $C_{12}$–$C_{14}$ fatty alcohol polyglycol ether having 7 EO units |
| Genapol ® O-150 methacrylate | $C_{16}$–$C_{18}$ fatty alcohol polyglycol ether methacrylate having 15 EO units |
| Genapol ® LA-250 crotonate | $C_{12}$–$C_{14}$ fatty alcohol polyglycol ether crotonate having 25 EO units |
| Genapol ® T-250 methacrylate | $C_{16}$–$C_{18}$ fatty alcohol polyglycol ether methacrylate having 25 EO units |
| Genapol ® T-250 acrylate | $C_{16}$–$C_{18}$ fatty alcohol polyglycol ether acrylate having 25 EO units |
| BB10 ® | polyoxyethylene(10)behenyl ether |
| TMPTA | trimethylolpropane triacrylate |
| Poly-NVP | poly-N-vinylpyrrolidone |
| Silvet ® 867 | siloxane-polyalkylene oxide copolymer |
| MBA | methylenebisacrylamide |
| AMA | allyl methacrylate |
| ®Y-12867 | siloxane-polyalkylene oxide copolymer |
| Silvet ® 7608 | polyalkylene oxide-modified heptamethyltrisiloxane |
| Silvet ® 7280 | polyalkylene oxide-modified heptamethyltrisiloxane |
| DADMAC | diallyldimethylammonium chloride |
| HEMA | 2-hydroxyethyl methacrylate |
| Quat | 2-(methacryloyloxy)ethyltrimethylammonium chloride |
| Fluowet ® AC 600 | perfluoroalkylethyl acrylate |
| Span ® 80 | sorbitan ester |

In one preferred embodiment the copolymers are water-soluble or water-swellable.

The described grafting of the copolymers with other polymers, which can be carried out optionally, leads to products having a particular polymer morphology and giving rise to optically clear gels in aqueous systems. A potential disadvantage of the copolymers without grafting is a more or less strong opalescence in aqueous solution. The basis for this opalescence is hitherto unavoidable, over-crosslinked polymer fractions which arise in the course of the synthesis and are inadequately swollen in water. This produces light-scattering particles whose size is well above the wavelength of visible light and which are therefore the cause of the opalescence. The described grafting process, which can be carried out optionally, substantially reduces or entirely prevents the formation of overcrosslinked polymer fractions in relation to conventional techniques.

The described incorporation both of cationic charges and of silicon, fluorine or phosphorus atoms into the copolymers, which can be carried out optionally, leads to products which in cosmetic formulations possess particular sensorial and rheological properties. An improvement in the sensorial and rheological properties may be of advantage in particular in the context of use in rinse-off products.

Silicon-modified copolymers may take over part or all of the functions of the silicone oils. The use of silicones can be reduced or avoided as a result of the copolymers.

Based on the finished compositions, the hair treatment compositions contain preferably from 0.01 to 10% by weight, more preferably from 0.1 to 5% by weight, very preferably from 0.5 to 3% by weight, of the copolymers.

As further auxiliaries and additives the hair treatment compositions may comprise oily substances, emulsifiers and coemulsifiers, cationic polymers, film formers, and also other additions customary in cosmetology, such as superfatting agents, moisturizing agents, stabilizers, active biogenic substances, glycerol, preservatives, pearlizing agents, dyes and fragrances, solvents, hydrotropic agents, opacifiers, further thickeners and dispersants, and also protein derivatives such as gelatin, collagen hydrolysates, natural or synthetic-based polypeptides, egg yolk, lecithin, lanolin and lanolin derivatives, fatty alcohols, silicones, substances with a keratolytic and keratoplastic action, enzymes and carrier substances, antioxidants, light stabilizers, UV light protection filters, active biogenic substances (local anesthetics, antibiotics, antiphlogistics, antiallergics, corticosteroids, sebostatics), active pharmaceutical substances and/or antidandruff agents.

An oily substance is any fatty substance which is liquid at room temperature (25° C.).

The fatty phase may therefore comprise one or more oils selected preferably from the following oils:

silicone oils, volatile or nonvolatile, linear, branched or cyclic, optionally with organic modification; phenylsilicones; silicone resins and silicone gums; mineral oils such as paraffin oil or vaseline oil; oils of animal origin such as perhydrosqualene, lanolin; oils of plant origin such as liquid triglycerides, e.g., sunflower oil, corn oil, soybean oil, rice oil, jojoba oil, babusscu oil, pumpkin oil, grapeseed oil, sesame oil, walnut oil, apricot oil, macadamia oil, avocado oil, sweet almond oil, lady's-smock oil, castor oil, triglycerides of caprylic/capric acids, olive oil, peanut oil, rapeseed oil, and coconut oil;

synthetic oils such as purcellin oil, isoparaffins, linear and/or branched fatty alcohols and fatty acid esters, preferably guerbet alcohols having 6 to 18, preferably 8 to 10, carbon atoms; esters of linear ($C_6$–$C_{13}$) fatty acids with linear ($C_6$–$C_{20}$) fatty alcohols; esters of branched ($C_6$–$C_{13}$) carboxylic acids with linear ($C_6$–$C_{20}$) fatty alcohols, esters of linear ($C_6$–$C_{18}$) fatty acids with branched alcohols, especially 2-ethylhexanol; esters of linear and/or branched fatty acids with polyhydric alcohols (such as dimerdiol or trimerdiol, for example) and/or guerbet alcohols; triglycerides based on ($C_6$–$C_{10}$) fatty acids;

esters such as dioctyl adipate, diisopropyl dimer dilinoleate; propylene glycols/dicaprylate or waxes such as beeswax, paraffin wax or microwaxes, alone or in combination with hydrophilic waxes, such as cetylstearyl alcohol, for example; fluorinated and perfluorinated oils; fluorinated silicone oils; mixtures of the aforementioned compounds.

Suitable nonionogenic coemulsifiers include adducts of from 0 to 30 mol of ethylene oxide and/or from 0 to 5 mol of propylene oxide with linear fatty alcohols having 8 to 22 carbon atoms, with fatty acids having 12 to 22 carbon atoms, with alkylphenols having 8 to 15 carbon atoms in the alkyl group, and with sorbitan or sorbitol esters; ($C_{12}$–$C_{18}$) fatty acid monoesters and diesters of adducts of from 0 to 30 mol of ethylene oxide with glycerol; glycerol monoesters and diesters and sorbitan monoesters and diesters of saturated and unsaturated fatty acids having 6 to 22 carbon atoms and, where appropriate, their ethylene oxide adducts; adducts of from 15 to 60 mol of ethylene oxide with castor oil and/or hydrogenated castor oil; polyol esters and especially polyglycerol esters, such as polyglyceryl polyricinoleate and polyglyceryl poly-12-hydroxystearate, for example. Likewise suitable are mixtures of compounds from two or more of these classes of substance.

Examples of suitable ionogenic coemulsifiers include anionic emulsifiers, such as mono -, di- or tri-phosphoric esters, but also cationic emulsifiers such as mono-, di-, and tri-alkyl quats and their polymeric derivatives.

Suitable cationic polymers include those compounds known under the INCI designation "Polyquaternium", especially Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, Polyquaternium 37&mineral oil&PPG trideceth (®Salcare SC95), PVP-dimethylaminoethyl methacrylate copolymer, guar-hydroxypropyltriammonium chlorides, and also calcium alginate and ammonium alginate.

It is additionally possible to employ cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as amidomethicones, for example; copolymers of adipic acid and dimethylaminohydroxypropyldiethylenetriamine; polyaminopolyamide and cationic chitin derivatives, such as chitosan, for example.

Examples of suitable silicone compounds are dimethylpolysiloxane, methylphenylpolysiloxanes, cyclic silicones, and amino-, fatty acid-, alcohol-, polyether-, epoxy-, fluoro- and/or alkyl-modified silicone compounds, and also polyalkylsiloxanes, polyalkylarylsiloxanes, polyethersiloxanes, as described in U.S. Pat. No. 5,104,645 and the documents cited therein, which at room temperature may be present either in liquid form or in resin form.

Suitable film formers, depending on the intended application, include salts of phenylbenzimidazolesulfonic acid, water-soluble polyurethanes, for example, $C_{10}$-polycarbamyl polyglyceryl esters, polyvinyl alcohol, polyvinylpyrrolidone, copolymers thereof, for example vinylpyrrolidone/vinyl acetate copolymer, water-soluble acrylic acid polymers/copolymers and their esters or salts, examples being partial ester copolymers of acrylic/methacrylic acid and polyethylene glycol ethers of fatty alcohols, such as acrylate/steareth-20 methacrylate copolymer, water-soluble cellulose, examples being hydroxymethylcellulose, hydroxyethylcellulose, hydroxypropylcellulose, water-soluble quaterniums, polyquaterniums, carboxyvinyl polymers, such as carbomers and their salts, polysaccharides, polydextrose for example, and glucan.

As superfatting agents it is possible to use substances such as, for example, lanolin and lecithin, unethoxylated and polyethoxylated or acylated lanolin derivatives and lecithin derivatives, polyol fatty acid esters, mono-, di-, and triglycerides, and/or fatty acid alkanol amides.

Moisturizers available include for example isopropyl palmitate, glycerol and/or sorbitol.

As stabilizers it is possible to use metal salts of fatty acids, such as magnesium, aluminum and/or zinc stearate, for example.

Active biogenic substances are to be understood as including, for example, plant extracts and vitamin complexes.

Additionally, the compositions of the invention may comprise organic solvents. Suitable organic solvents include in principle all monohydric or polyhydric alcohols. Preference is given to using alcohols having 1 to 4 carbon atoms such as ethanol, propanol, isopropanol, n-butanol, isobutanol, t-butanol, glycerol, and mixtures of said alcohols. Further preferred alcohols are polyethylene glycols having a relative molecular mass of less than 2000. Particular preference is given to the use of polyethylene glycol having a relative molecular mass of between 200 and 600 in amounts of up to 45% by weight and of polyethylene glycol having a relative molecular mass of between 400 and 600 in amounts of from 5 to 25% by weight. Further suitable solvents are, for example, triacetin (glyceryl triacetate) and 1-methoxy-2-propanol. A hydrotropic action is developed by short-chain anionic surfactants, especially arylsulfonates, for example, cumene sulfonate or toluene sulfonate.

The compositions of the invention can be blended with conventional ceramides, pseudoceramides, fatty acid N-alkylpolyhydroxyalkyl amides, cholesterol, cholesterol fatty acid esters, fatty acids, triglycerides, cerebrosides, phospholipids, and similar substances as a care additive.

Suitable UV filters include for example 4-aminobenzoic acid; 3-(4'-trimethylammonium)benzylideneboran-2-one methylsulfate; 3,3,5-trimethylcyclohexyl salicylate; 2-hydroxy-4-methoxybenzophenone; 2-phenylbenzimidazole-5-sulfonic acid and its potassium, sodium, and triethanolamine salts; 3,3'-(1,4-phenylenedimethine)bis(7,7-dimethyl-2-oxobicyclo[2.2.1]heptane-1-methanesulfonic acid and its salts; 1-(4-tert-butylphenyl)-3-(4-methoxyphenyl)propane-1,3-dione, 3-(4'-sulfo)-benzylidenebornan-2-one and its salts; 2-ethylhexyl 2-cyano-3,3-diphenylacrylate; polymer of N-[2(and 4)-(2-oxoborn-3-ylidenemethyl)benzyl]acrylamide; 2-ethylhexyl 4-methoxycinnamate; ethoxylated ethyl 4-aminobenzoate; isoamyl 4-methoxycinnamate; 2,4,6-tris[p-(2-ethylhexyloxycarbonyl)anilino]-1,3,5-triazine; 2-(2H-benzotriazol-2-yl)-4-methyl-6-(2-methyl-3-(1,3,3,3-tetramethyl-1-(trimethylsilyloxy)disiloxanyl)propyl)phenol; 4,4'-[(6-[4-((1,1-dimethylethyl)aminocarbonyl)phenylamino]-1,3,5-triazin-2,4-yl)diimino]bis(benzoic acid 2-ethylhexyl ester); 3-(4'-methylbenzylidene)-D,L-camphor; 3-benzylidenecamphor; 2-ethylhexyl salicylate; 2-ethylhexyl 4-dimethylaminobenzoate; hydroxy-4-methoxybenzophenone-5-sulfonic acid (sulisobenzone) and the sodium salt; and/or 4-isopropylbenzyl salicylate.

Examples of suitable antioxidants include superoxide dismutase, tocopherol (vitamin E), and ascorbic acid (vitamin C).

Examples of suitable preservatives include phenoxyethanol, parabens, pentanediol or sorbic acid.

As dyes it is possible to use the substances which are suitable and approved for cosmetic purposes.

Suitable antidandruff agents and active antifungal substances (fungicides) include preferably ketoconazole, Climbazol®, Octopirox®, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, Zn pyrithione, and octopirox.

Active biogenic substances which can be used include for example Bisabolol®, Allantoin®, Phytantriol®, Panthenol®, AHA acids, plant extracts, and vitamin complexes.

As acids and alkalis for adjusting pH it is preferred to use citric acid and/or sodium hydroxide solution.

The compositions are normally adjusted to a pH in the range from 2 to 12, preferably from 3 to 8.

The overall fraction of auxiliaries and additives in the hair treatment compositions is preferably from 1 to 30% by weight, more preferably from 2 to 20% by weight.

Preferred embodiments are rinses, cures, spray cures, lotions, creams, gels, foams, and sprays.

The examples and applications which follow are intended to illustrate the invention, though without restricting it thereto (all percentages are by weight). The copolymers used in the examples are representatives of the particularly preferred copolymers 1 to 67 already listed in the description. They were prepared by the therein-indicated processes 1, 2, 3 or 4 using the preferred initiators and solvents.

EXAMPLE 1

Hair Rinse

| | | |
|---|---|---|
| I) | Genaminox CSL | 6.0% |
| | Cetiol HE | 2.0% |
| II) | Copolymer No. 48 | 1.2% |
| III) | Water | ad 100% |

To prepare the hair rinses 1 a mixture 1 is prepared in each case from the components under I). For that purpose the components under I) are dissolved with stirring at approximately RT until the solution clarifies. Then the mixture 1 is cooled to room temperature. To prepare a mixture 2 in each case component II) is dispersed in component III) and the mixture is stirred until it clarifies. Subsequently mixtures 1 and 2 are mixed with one another with stirring. Thereafter the pH is adjusted to about 4 by means of citric acid.

EXAMPLE 2

Hair Rinse

| | | |
|---|---|---|
| I) | Cetyl alcohol | 3.0% |
| | Hostaphat KL 340 D | 1.5% |
| | Liquid paraffin nv | 0.5% |
| II) | Copolymer No. 35 | 1.0% |
| III) | Water | ad 100% |

To prepare the hair rinse 2 the components under I are melted at about 75° C. (mixture 1). II) is swollen in III) with stirring and then heated to about 75° C. (mixture 2). Thereafter mixture 2 is added to mixture 1 with stirring. The mixture is cooled to room temperature with stirring.

Finally, adjust the pH to about 4.

EXAMPLE 3

Hair Spray Cure

| | | |
|---|---|---|
| I) | Copolymer No. 49 | 2% |
| | Genaminox CS | 4% |
| | Cetiol HE | 2% |
| | Panthenol | 0.2% |
| II) | Water | ad 100% |

To prepare the hair spray cure a mixture is prepared in each case from components I) and II). For this purpose the components under I) are dissolved with stirring in component II) until the solution clarifies. Subsequently the mixture is cooled to room temperature. Thereafter the pH is adjusted to about 4 by means of citric acid.

EXAMPLE 4

Hair Cure

| | |
|---|---|
| Genamin KSL | 7% |
| Hostaphat KL 340 D ® | 1.5% |
| Genapol PDC ® | 4% |
| Copolymer No. 60 | 1.7% |
| Liquid paraffin nv | 1% |
| Jojoba oil | 1% |
| Propylene glycol | 0.8% |
| Isopropyl palmitate | 1% |
| Dow Corning 190 ® | 0.8% |
| Extrapon | 0.3% |
| Vitamin E | 0.3% |
| Panthenol (vitamin B 5) | 0.5% |

Preparation is carried out in the successive steps I to VI:
I Swell polymer in water at RT with stirring.
II Melt oil phase containing oil/s, quats, solubilizers and, where appropriate, vitamins at about 75° C.
III Heat water phase (I) to about 75° C.
IV Add water phase (I) to the oil phase (II) and stir cold.
V At about 30° C. add pearlescence concentrate, optionally dye, fragrance, and plant extracts.
VI Adjust pH.

EXAMPLE 5

Hair Rinse

| I) Genamin CTAC | 5.0% |
|---|---|
| Genamin KDMP | 0.5% |
| Genaminox LA | 5.0% |
| Velsan D8P-3 | 1.0% |
| II) Water | 27.3% |
| III) Copolymer No. 41 | 1.2% |
| IV) Water | ad 100% |

To prepare the hair rinses from examples 1 to 5 in each case a mixture 1 is prepared from components I) and II). For this purpose component I) is dissolved in component II) with stirring at about 60° C. until the solution clarifies. Subsequently mixture 1 is cooled to room temperature. To prepare a mixture 2 in each case component III) is dispersed in component IV) and the mixture is stirred until it clarifies. The mixtures 1 and 2 are subsequently mixed with one another with stirring. Thereafter the pH is adjusted to about 4 by means of citric acid.

INCI designation of the commercial products used:

| Genamin KSL ® | (Clariant) | PEG-5 stearyl ammonium lactate |
|---|---|---|
| Genapol PDC ® | (Clariant) | glycol distearate (and) laureth-4 (and) cocamidopropylbetaine (and) mica (and) titanium dioxide |
| Hostaphat KL 340 D ® | (Clariant) | trilaureth-4 phosphate |
| Dow Corning 190 ® | (Dow Corning) | dimethicone copolyol |
| Extrapon ® | (Dragoco) | plant extracts |
| Genaminox LA | (Clariant GmbH) | lauryldimethylamine oxide |
| Genaminox CSL | (Clariant GmbH) | cocamine oxide |
| Genapol UD-80 | (Clariant GmbH) | undeceth-8 |
| Velsan D8P-3 | (Clariant GmbH) | isopropyl PPG-2-isodeceth-7 carboxylate |
| Cetiol HE | (Henkel) | PEG-7 glyceryl cocoate |
| Genagen CA-050 | (Clariant GmbH) | PEG-5 cocamide |
| Genamin KDM-P ® | (Clariant) | behenyltrimethylammonium chloride |
| Genamin CTAC ® | (Clariant) | cetyltrimethylammonium chloride |

What is claimed is:

1. A cosmetic or dermatological hair treatment composition which comprises at least one copolymer obtained by free-radical copolymerization of
   A) acryloyldlmethyltaurine and/or acryloyldimethyltaurates,
   B) optionally, one or more further olefinically unsaturated, noncationic, comonomer which have at least one oxygen, nitrogen, sulfur or phosphorus atom and possess a molecular weight of less than 500 g/mol,
   C) optionally, one or more olefinically unsaturated, cationic comonomer which have at least one oxygen, nitrogen, sulfur or phosphorus atom and possess a molecular weight of less than 500 g/mol,
   D) optionally, one or more silicon-containing component capable of free-radical polymerization and having a functionality of at least one,
   E) optionally, one or more fluorine-containing component capable of free-radical polymerization and having a functionality of at least one,
   F) one or more olefinically mono- or polyunsaturated, macromonomer each possessing at least one oxygen, nitrogen, sulfur or phosphorus atom and having a number-average molecular weight of greater than or equal to 200 g/mol, the macromonomer not being the silicon-containing component D) or fluorine-containing component E), and where at least one macromonomer F) is a compound of formula(IV)

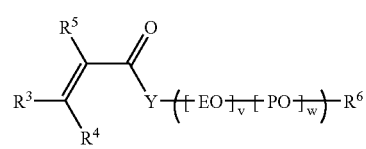

(IV)

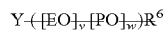

(IV)

wherein $R^3$, $R^4$, $R^5$, and $R^6$ are independently of one another hydrogen or n-aliphatic $(C_1-C_{30})$ hydrocarbon, iso-aliphatic $(C_1-C_{30})$ hydrocarbon, olefinic $(C_1-C_{30})$ hydrocarbon, cycloaliphatic $(C_1-C_{30})$ hydrocarbon, arylaliphatic $(C_1-C_{30})$ hydrocarbon, or aromatic $(C_1-C_{30})$ hydrocarbon radical;

EO is an ethylene oxide unit;

PO is a propylene oxide unit;

Y is a chemical bridge;

v and w independently of one another amount to from 0 to 500, the sum of v and w being on average $\geq 1$; and G) optionally, the copolymerization taking place in the presence of at least one polymeric additive having number-average molecular weights of from 200 g/mol to $10^9$ g/mol, H) with the proviso that component A) is copolymerized with at least one component selected from one of component D) to G).

2. The hair treatment composition as claimed in claim 1, wherein the comonomer B) is selected from the group consisting of unsaturated carboxylic acids, salts of unsaturated carboxylic acids, anhydrides of unsaturated carboxylic acids, esters of unsaturated carboxylic acids with aliphatic, olefinic, cycloaliphatic, arylaliphatic or aromatic alcohols having 1 to 22 carbon atoms, open-chain N-vinyl amides, cyclic N-vinyl amides having a ring size of from 3 to 9, amides of acrylic acid, amides of methacrylic acid, amides of substituted acrylic acids, amides of substituted methacrylic acids, 2-vinylpyridine, 4-vinylpyridine, vinyl acetate; styrene, acrylonitrile, vinyl chloride, vinylidene chloride, tetrafluoroethylene, vinylphosphonic acid or the esters or salts thereof, vinylsulfonic acid or the esters or salts thereof, allylphosphonic acid or the esters or salts thereof, methallylsulfonic acid or the esters or salts thereof, and mixtures thereof.

3. The hair treatment composition as claimed in claim 1, wherein the comonomer C) is selected from the group consisting of
diallyldimethylammonium chloride (DADMAC),
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride,
N-methyl-4-vinylpyridinium chloride,
dimethylaminoethyl methacrylate,
dimethylaminopropylmethacrylamide,
methacryloylethyl N-oxide,
methacryloylethylbetaine, and mixtures thereof.

4. The hair treatment composition of claim 1, wherein the silicon-containing component D) is a compound of formula (I)

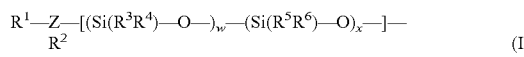

where
$R^1$ is a radical selected from the group consisting of vinyl, allyl, methallyl, methylvinyl, acryloyl, methacryloyl, crotonyl, seneclonyl, itaconyl, maleyl, fumaryl, styryl, and mixtures thereof;
Z is a chemical bridge;
$R^3$, $R^4$, $R^5$, and $R^6$ independently of one another are —$CH_3$, —O—$CH_3$, —$C_8H_5$ or —O—$C_6H_5$;
w, x denote numbers from 0 to 500, it being necessary for either w or x to be greater than zero; and
$R^2$ is a saturated or unsaturated aliphatic, cycloaliphatic, arylaliphatic or aromatic radical having in each case 1 to 50 carbon atoms or a group of the formulae —OH, —$NH_2$, —$N(CH_3)_2$, —$R^7$ or a group —Z—$R^1$, where Z and $R^1$ have the meanings mentioned above, and
$R^7$ is selected from the group consisting of —O—Si($CH_3$)$_3$, —O—Si(phenyl)$_3$, —O—Si(O—Si($CH_3$)$_3$)$_2$$CH_3$) and —O—Si(O—Si(phenyl)$_3$)$_2$phenyl).

5. The hair treatment composition of claim 1, wherein the fluorine-containing components E) are compounds of the formula (II)

where
$R^1$ is a polymerizable function from a vinylically unsaturated compound;
Y is a chemical bridge, and
r, s are stoichiometric coefficients which independently of one another can be numbers between 0 to 200.

6. The hair treatment composition of claim 1, wherein the polymeric additive G) is selected from the group consisting of polyalkylene glycol, alkylpolyglycol, and mixtures thereof or a homopolymer or copolymer of a compound selected from the group consisting of N-vinylformamide, N-vinylacetamide, N-vinylpyrrolidone, ethylene oxide, propylene oxide, acryloyldimethyltaurine, N-vinylcaprolactone, N-vinylmethylacetamide, acrylamide, acrylic acid, methacrylic acid, N-vinylmorpholide, hydroxymethyl methacrylate, diallyldimethylammonium chloride (DADMAC), [2-(methacryloyloxy)ethyl]trimethylammonium chloride (MAPTAC), and mixtures thereof.

7. The hair treatment composition of claim 1, wherein the copolymerization takes place in the presence of at least one polymeric additive G).

8. The hair treatment composition of claim 1, wherein the copolymers are crosslinked.

9. The hair treatment composition of claim 1, wherein the copolymers are prepared by precipitation polymerization in tert-butanol.

10. The hair treatment composition of claim 1, wherein the copolymers are water-soluble or water-swellable.

11. The hair treatment composition of claim 1, which comprises, based on the finished composition, from 0.01 to 10% by weight of the copolymers.

12. The hair treatment composition of claim 1, further comprising oily substances, emulsifiers, coemulsifiers, cationic polymers, film formers, superfatting agents, moisturizers, stabilizers, glycerol, preservatives, pearlizing agents, dyes and fragrances, solvents, hydrotropic agents, opacifiers, thickeners, dispersants, protein derivatives, polypeptides on a natural or synthetic basis, egg yolk, lecithin, lanolin, lanolin derivatives, fatty alcohols, silicones, substances having a keratolytic and keratoplastic effect, enzymes, carrier substances, antioxidants, light stabilizers, UV light protection filters, active biogenic substances, active pharmaceutical substances, antidandruff agents, and mixtures thereof.

13. The hair treatment composition of claim 1, which is a rinse, cure, spray cure, lotion, cream, gel, foam or spray.

14. The hair treatment composition of claim 1 wherein, $R^1$ is a vinylically unsaturated compound selected from the group consisting of a vinyl, allyl, methallyl, methylvinyl, acryloyl, methacryloyl, crotonyl, seneclonyl, itaconyl, maleyl, fumaryl, styryl radical, and mixtures thereof.

15. The hair treatment composition of claim 1, wherein the bridging group Y is selected from the group consisting of —O—, —S—, —C(O)—, —C(O)—O—, —O—$CH_2$—CH(O—)—$CH_2$OH, —O—$CH_2$—CH(OH)—$CH_2$O—, —O—$SO_2$—O—, —O—SO—O—, —PH—, —P($CH_3$)—, —$PO_3$—, —NH—, —N($CH_3$)—, and mixtures thereof.

16. The hair treatment composition of claim 1, wherein the discrete repeating units of A, B, C, and D are originating from a unit selected from the group consisting of acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

17. The hair treatment composition of claim 1, wherein the discrete repeating units of A, B, C, and D are originating from a unit of ethylene oxide or propylene oxide.

18. The hair treatment composition of claim 1, wherein v, w, x, and z independently of one another amount to from 1 to 30.

19. The hair treatment composition of claim 4, wherein the chemical bridge, Z, is selected from the group consisting of —O—, —(($C_1$–$C_{50}$)alkyl)—, —(($C_6$–$C_{30}$)aromatic)-, —(($C_5$–$C_8$)cycloalkyl)-, —(($C_1$–$C_{50}$)alkenyl)-, -(polypropylen oxide)$_n$—, —(polyethylene oxide)$_o$—, —(polypropylene oxide)$_m$(polyethylene oxide)$_o$—, and mixtures thereof, wherein n and o independently of one another denote numbers from 0 to 200, and the distribution of the ethylene oxide(propylene oxide units can be random or in block form.

20. The hair treatment composition of claim 5 wherein the chemical bridge, Z, is —(($C_1$–$C_{10}$)alkyl)—(Si(OCH$_3$)$_2$)—, or —(Si(OCH$_3$)$_2$)—.

21. The hair treatment composition of claim 5 wherein, $R^1$ is a radical selected from the group consisting of vinyl, allyl, methallyl, methylvinyl, acryloyl, methacryloyl, crotonyl, seneclonyl, itaconyl, maleyl, fumaryl, styryll, and mixtures thereof.

22. The heir treatment composition of claim 5, wherein the chemical bridge Y is selected from the group consisting of —O—, —C(O)—, —C(O)—O—, —S—, —O—CH$_2$—CH(O—)—CH$_2$OH, —O—CH$_2$—CH(OH)—CH$_2$—O—, —O—SO$_2$—O—, —O—S(O)—O—, —PH—, —P(CH$_3$)—, —PO$_3$—, —NH—, —N(CH$_3$)—, —O—(C$_1$–C$_{50}$)alkyl-O—, —O phenyl-O—, —O-benzyl—O—, —O—(C$_5$–C$_8$)cycloalkyl-O—, —O—(C$_1$–C$_{50}$)alkenyl-O—, —O—(CH(CH$_3$)—CH$_2$—O)$_n$—, —O—(CH$_2$—CH$_2$—O)$_n$——O—([CH—CH$_2$—O]$_n$—[CH$_2$-CH$_2$—O]$_m$)$_o$—, where n, m, and o independently of one another denote numbers from 0 to 200, and mixtures thereof.

23. The cosmetic or dermatological hair treatment composition of claim 1, wherein in formula (IV) R$^3$, R$^4$ and R$^5$ are H or —CH$_3$.

24. The cosmetic or dermatological hair treatment composition of claim 1, wherein in formula (IV) R$^3$ and R$^4$ are H.

25. The cosmetic or dermatological hair treatment composition of claim 1, wherein in formula (IV) the sum of v and w is from 1 to 30.

26. The cosmetic or dermatological hair treatment composition of claim 1, wherein In formula (IV) the EO and PO units are distributed in a distribution selected from the group consisting of random, block, alternating, gradient, and combinations thereof.

* * * * *